United States Patent [19]

Fermani et al.

[11] Patent Number: 5,475,984
[45] Date of Patent: Dec. 19, 1995

[54] METHOD AND APPARATUS FOR PRODUCING FROZEN PARTICLES USING AN ENTRAPMENT ZONE OF ATOMIZED CRYOGENIC LIQUID DROPLETS

[75] Inventors: Nicholas R. Fermani; Mark G. Fletcher, both of Newark, Del.

[73] Assignee: E. I. Du Pont de Nemours and Company, Wilmington, Del.

[21] Appl. No.: 298,231

[22] Filed: Aug. 29, 1994

Related U.S. Application Data

[63] Continuation of Ser. No. 49,819, Apr. 20, 1993, abandoned.

[51] Int. Cl.$^6$ ................................................ F25D 17/02
[52] U.S. Cl. .................................................. 62/64; 62/373
[58] Field of Search ................................. 62/64, 373

[56] References Cited

U.S. PATENT DOCUMENTS 3,004,406 10/1961 Foote et al. .
4,568,369 2/1986 Destruhaut ........................ 62/64
4,623,706 1/1986 Timm et al. ....................... 526/88
5,196,049 2/1993 Coombs et al. .................. 75/338

FOREIGN PATENT DOCUMENTS

0468269A1 7/1991 European Pat. Off. .
0478118A1 7/1991 European Pat. Off. .
1559920 12/1977 Germany .
681461 4/1970 Netherlands .

Primary Examiner—Ronald C. Capossela

[57] ABSTRACT

This invention relates to an apparatus and process for producing frozen particles of a liquid product having a liquid product nozzle for introducing liquid product droplets to be frozen and a plurality of cryogenic nozzles for introducing a cryogenic liquid directed away from the liquid product droplets.

13 Claims, 5 Drawing Sheets

METHOD AND APPARATUS FOR PRODUCING FROZEN PARTICLES USING AN ENTRAPMENT ZONE OF ATOMIZED CRYOGENIC LIQUID DROPLETS

This is a continuation of application Ser. No. 08/049,819 filed Apr. 20, 1993 now abandoned.

FIELD OF THE INVENTION

This invention relates to an apparatus and method for producing frozen particles of a liquid and, more particularly, to an apparatus having a liquid nozzle for introducing liquid droplets to be frozen and a plurality of flat spray cryogenic nozzles for creating an entrapment zone of atomized droplets of cryogenic fluid so as to freeze the liquid droplets to produce frozen particles.

BACKGROUND ART

The formation of physically uniform and chemically homogeneous spherical frozen particles from aqueous biological solutions and suspensions is essential to the manufacture of unit dose tablets for the pharmaceutical and diagnostic industries. Physically uniform particles minimize variability in bulk density and provide for tablet manufacturing processes that can produce tablets which vary in weight by no more than about one percent. Homogeneous chemical composition of the particles is needed to insure an accurate unit dose. From a manufacturing perspective it is desirable for frozen particles which are processed in various types of manufacturing tablet making equipment to exhibit the free flow properties characteristic of spherical particles. Furthermore, any manufacturing process for obtaining frozen particles with these desired characteristics should operate efficiently to offset the generally high cost of reagents and other raw materials.

Known techniques used in processing granular products include dry blending, direct compression, wet granulation, particle fabrication by coating product nuclei with discrete ingredient, fluidized bed granulation and spray freezing of frozen particles.

Spray freezing methods generally produce highly uniform particles as a result of their characteristically rapid freezing processes. However, spray freezing is generally an expensive technique due to the high cost of refrigerants and the relatively large product losses which can occur.

Typical methods of spray freezing include striking or impinging a solution to be frozen into or against a liquid refrigerant stream(s) or spray(s), spraying a solution to be frozen onto the surface of a bath of liquid refrigerant, and spraying solution to be frozen through a freezing zone. Examples of refrigerants typically used to accomplish this freezing include liquid nitrogen, liquid carbon dioxide, and fluorocarbons. Some of the disadvantages of these known methods are: insufficient throughput to support manufacturing sale needs, loss of product due to partial freezing and/or accumulation on the sides of the freeze chamber, and inefficient uses of cryogenic liquids.

German Patent No. 2,556,790 filed on Nov. 20, 1972 and published Jun. 6, 1974 discloses a process for deep freezing aqueous extracts with a freezing vessel having a conical lower section which provides for the impingement of a liquid product with a liquid refrigerant. Impingement occurs by one of three disclosed variations including downwardly spraying product and upwardly spraying refrigerants, upwardly spraying both product and liquid refrigerant, and both upwardly and downwardly spraying the product and upwardly spraying the liquid refrigerant. The disadvantage of this apparatus is the likelihood that frozen product will adhere to the liquid refrigerant nozzles and the funnel shaped bottom of the spray chamber, thus resulting in yield losses.

U.S. Pat. No. 4,952,224, issued Aug. 28, 1990, discloses an apparatus having a downwardly directed spray of atomized liquid fat and a radially inwardly directed plurality of individual spray jets of liquid nitrogen or carbon dioxide which surround and impinge against the downwardly directed spray of liquid fat droplets. The individual spray jets of this apparatus are likely to produce non-uniform agglomerations of the product due to the high velocity contact of the liquid refrigerant and the product. In addition, due to the limited time that the product is in contact with the liquid refrigerant, at least some product is unlikely to be frozen.

Italian Patent No. 2,659,546 issued Jul. 18, 1985, discloses an apparatus for freezing food products having an insulated freezing chamber with a conical lower section and a liquid refrigerant nozzle with a vertically downward directed spray located in the top center of the chamber. A plurality of product nozzles are distributed around and directed at the sides of the central refrigerant spray. Using this apparatus it is likely that unacceptably high particle size variations would occur during a continuous manufacturing process due to variations likely to occur in product supply and control systems, such as pressure changes in the product supply pump and pulsations within the nozzles.

There is needed an apparatus and process for producing uniformly, shaped, homogeneous frozen particles of a liquid, capable of supporting full scale manufacturing needs, which minimizes product yield losses due to accumulation of product on the inside of the freeze chamber and partially frozen particles.

SUMMARY OF THE INVENTION

Many of the disadvantages of the prior art are solved by the apparatus and process of the present invention. The apparatus and method of the present invention allow for the production of physically uniform and chemically homogeneous particles in a way that maximizes throughput or product yield and minimizes loss of product due to partial freezing and/or accumulation on the inner walls of the apparatus, and further minimizes the efficient use of cryogenic liquid. By physically uniform is meant of substantially the same size, shape and density.

This invention relates to an apparatus for utilizing a cryogenic liquid for producing frozen particles of a liquid product which comprises:

(a) a housing;

(b) means including at least three cryogenic liquid nozzles for producing a substantially continuous, annular downwardly directed circumferential wall of cryogenic liquid defining an interior entrapment zone; and (c) a liquid product nozzle positioned in the housing for introducing droplets of the liquid product into the entrapment zone whereby the cryogenic liquid freezes the liquid product droplets to produce frozen particles.

Yet another aspect of the invention relates to a process for utilizing a cryogenic liquid for producing frozen particles of a liquid product in a housing which comprises the steps of:

(a) introducing the cryogenic liquid into the housing in an annular, downward direction creating an substantially continuous downwardly directed circumferential wall of cryogenic liquid, defining an interior entrapment zone; and (b) introducing droplets of the liquid product into the entrapment zone, whereby the cryogenic liquid freezes the liquid product droplets to produce frozen particles.

The apparatus and process of the present invention offer significant advantages over the prior art by providing highly uniform, homogeneous frozen particles with minimum process yield losses. Yield losses are minimized during operation of the apparatus of the present invention in that the configuration of the cryogenic liquid nozzles form the sides of an entrapment zone of droplets of cryogenic liquid into which the liquid product droplets are introduced. The entrapment zone is created by introducing the cryogenic liquid into the housing in a downwardly directed planar spray pattern, using at least three cryogenic liquid nozzles. The liquid product droplets are contained within the entrapment zone, and directed in a downward direction such that the liquid product droplets do not impinge upon or break through the walls of the entrapment zone.

DESCRIPTION OF THE PREFERRED EMBODIMENT OF THE INVENTION

Figure 1:
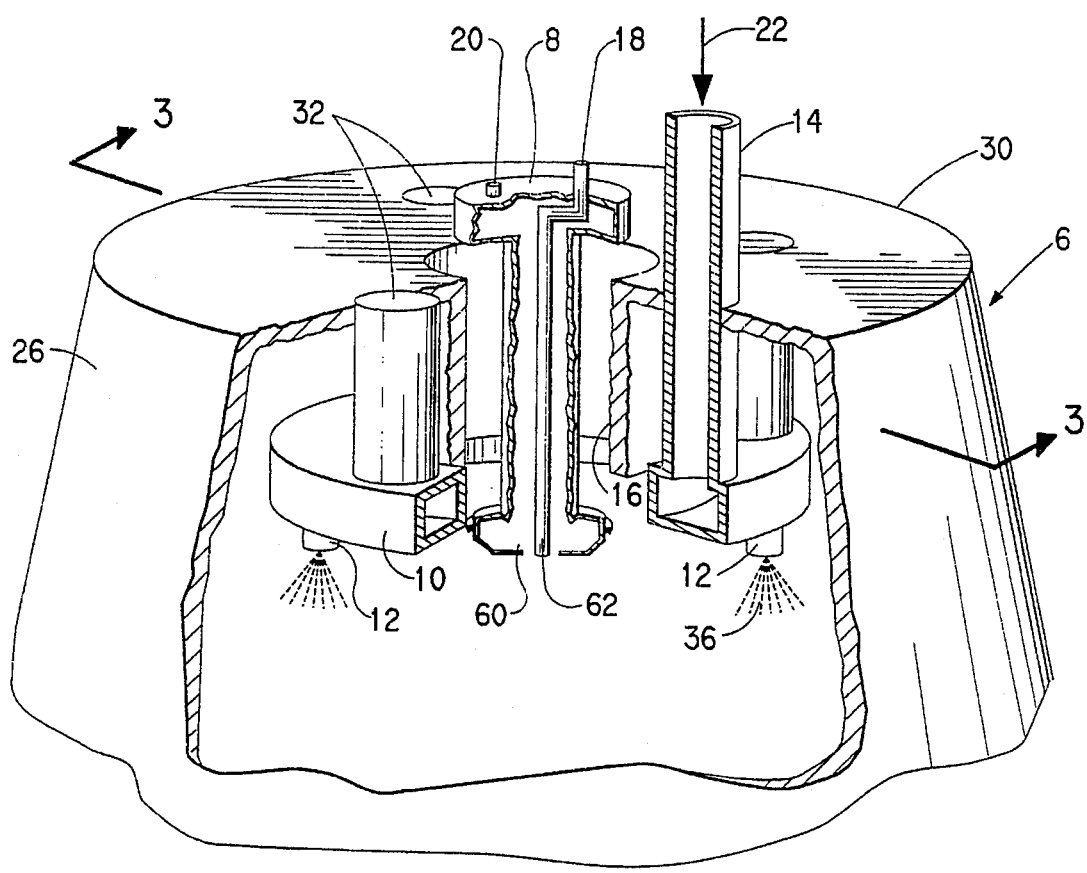
FIG. 1 is a perspective view, partially cut away, of an upper portion of an apparatus constructed in accordance with a preferred embodiment of this invention for producing frozen particles of a liquid.
Figure 2:
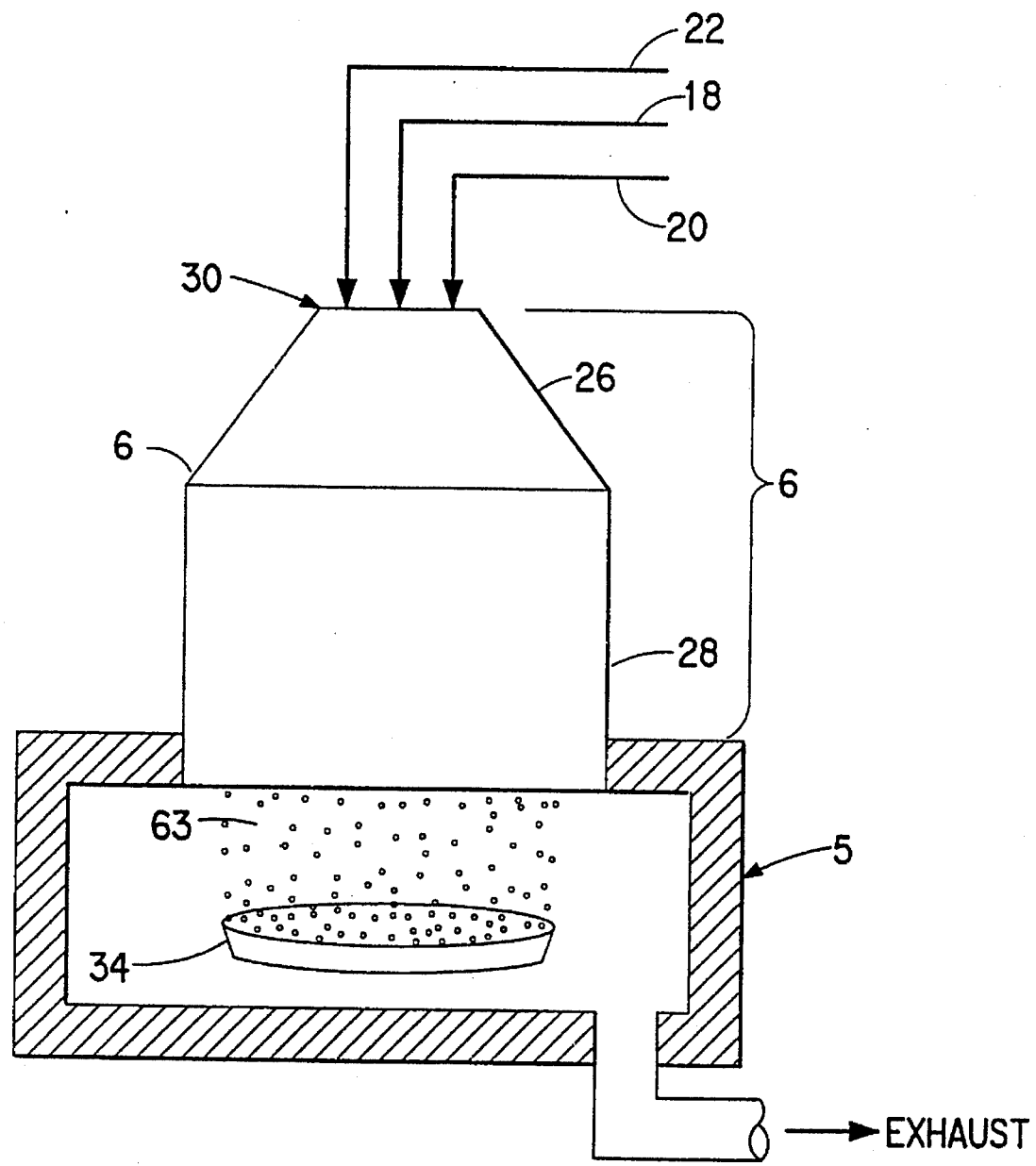
FIG. 2 is a partially schematic representation of an apparatus for producing frozen particles using the apparatus of FIG. 1.

There may be seen in FIGS. 1 and 2, preferred embodiment of an apparatus constructed in accordance with this invention for producing frozen particles of a liquid product, the apparatus comprises a generally cylindrical housing 6, a liquid product nozzle, such as an atomization nozzle 8, for introducing droplets of the liquid to be frozen, and a plurality of cryogenic liquid nozzles 12 for introducing a cryogenic liquid into the housing 6 in a manner that directs the cryogenic liquid in a downward direction to form an entrapment zone or curtain cryogenic liquid droplets 36, whereby the cryogenic liquid freezes the liquid product droplets 63 to produce frozen particles.

Figure 3:
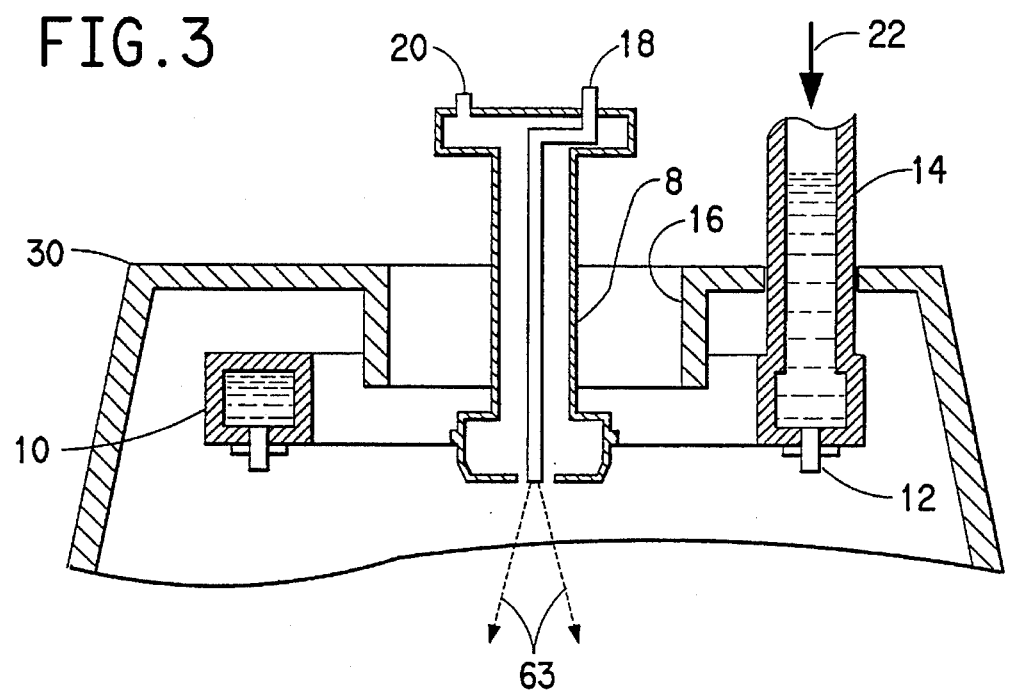
FIG. 3 is a cross section of FIG. 1 taken along the section lines 3—3 depicting the upper portion of the apparatus for producing frozen particles.
Figure 4C:
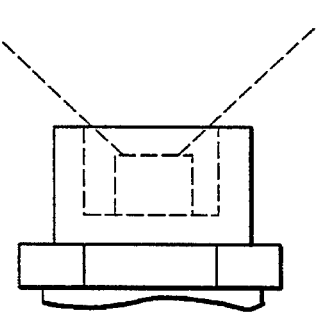
FIGS. 4a, 4b, and 4c are partially schematic representations of various views of a cryogenic liquid nozzle.
Figure 4B:
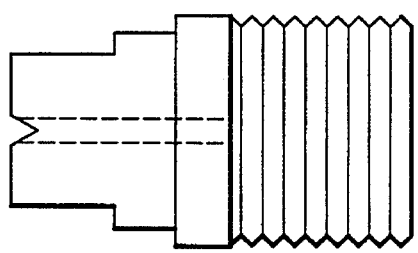
Figure 4A:
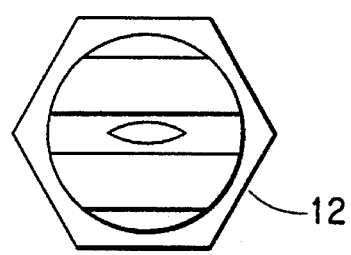

FIGS. 1 and 3 depict an atomization nozzle 8 suitable for use as the liquid product nozzle of the present invention. Such atomization nozzles 8 are known in the art and are available commercially. The atomization nozzle 8 is directed downwardly into the housing 6 so as to discharge liquid product in a vertically downward direction and designed so that a gas from a source not shown, but depicted by arrow 20, such as nitrogen or air, is forced under pressure through an annular channel 60, which surrounds a centrally located tube 62, through which the liquid product, shown by arrow 18, is discharged under pressure, such that the gas 20 breaks up the discharging liquid product into the liquid product droplets 63. Nitrogen is the preferred inert gas for use in the atomization nozzle 8. The end of the atomization nozzle 8 through which the liquid product is discharged is tapered inwardly providing a thin annulus through which the gas escapes at high velocity disposed about the liquid product. Such atomization nozzles 8 are generally useful for producing droplets in the size range of about 8 to about 4300 μm.

Several examples of known types of droplet forming nozzles or atomization nozzles can be used as the liquid product nozzle, including ultrasonic nozzles, hydraulic nozzles, and pneumatic nozzles. An example of a suitable ultrasonic nozzle for use in the present invention is the Model 8700 nozzle available from Sono-Tek Corp., Poughkeepsie, N.Y. and an example of a suitable hydraulic nozzle is Model SU-5 available from Spraying Systems Co. (Wheaton, Ill.). Pneumatic nozzles are preferred.

Referring to FIGS. 1 and 2, the preferred housing 6 has an upper plate 30 and a vertically disposed cylinder 28 having a diameter larger than the diameter of the upper plate 30, the upper plate 30 and cylinder 28 connected by a truncated conical section 26 having an upper conical diameter the same as the diameter of the upper plate 30 and a lower conical diameter the same as the lower diameter of the cylinder 28.

The diameter of the upper plate 30 should be sufficiently large to allow for the presence of a plurality of cryogenic liquid nozzles 12, the liquid product nozzle, such as an atomization nozzle 8, and a baffle 16 (if used) between the plurality of cryogenic liquid nozzles 12 and the liquid product nozzle.

The truncated conical section 26 should preferably be designed so that it is of sufficient length to allow for the formation of the entrapment zone of cryogenic liquid droplets.

The lower diameter of the cylinder 28 is defined by the lower conical diameter of the truncated conical section 26 and the cylinder should be of sufficient length to enclose and direct the frozen product particles and any gaseous cryogen which may have evaporated from the cryogenic liquid into the lower end of the cylinder 28 of the housing 6.

Preferably the apparatus is provided with a collection means 34 for the frozen particles. Any collection means 34 large enough to capture and hold the frozen particles produced in the housing 6 can be used including relatively simple devices such as trays which are manually operated as well as fully automated conveyor type systems for transporting the frozen particles away from the apparatus of the invention. The collection means 34 should be kept at a temperature below the freezing point of the frozen particles to insure that the frozen particles do not melt; such a temperature can be maintained, preferably, using the cooling effect resulting from the evaporation of cryogenic liquid to gaseous cryogen.

Preferably, a baffle 16 is included between the cryogenic liquid nozzles 12 and the atomization nozzle 8. Such a baffle 16 serves to shield the liquid product nozzle 8 from the cryogenic liquid introduced into the housing 6 by the cryogenic liquid nozzles 12. The baffle 16 can be supported by any means sufficient to hold it between the atomization 8 and the cryogenic liquid nozzles 12 and should extend between the atomization nozzle 8 and the liquid cryogen nozzles 12 to a depth sufficient to shield the product nozzle 8.

By "liquid product" is meant any liquid which is to be frozen into uniform spherical particles. The preferred liquid products are aqueous solutions useful as diagnostic reagents or pharmaceutical reagents, including but not limited to solutions containing dissolved proteins such as enzymes, antibodies, antigens, vitamins, and hormones, solutions of other biological materials such as nucleic acids, antibiotics, and various drugs. Examples of such diagnostic reagents include aqueous solutions of biologically active substances such as nicotinamide adenine dinucleotide (NAD), which can be used in toxicology testing for analytically determining lactic acid and ethyl alcohol, and NAD-reduced disodium salt trihydrate (NADH), which can be used in analytically determining alpha-hydroxybutyrate dehydrogenase, the amount of which in turn can be related to the amount of the isoenzymes LD1 and LD2 of lactate dehydrogenase (LDH). These biologically active substances are preferably combined with an excipient such as mannitol or trehalose, and a lubricant such as carbowax. Other examples of suitable liquid products for use as diagnostic reagents and which can be frozen in accordance with the present invention include solutions of indicator compounds such as the organic dye dichloroindophenol, useful in determining pseudocholinesterase (PCHE), and liquid suspensions such as for example, a slurry of creatine kinase MB (CKMB) monoclonal antibody-coated chromium dioxide particles suspended in water, which can be used to test for the MB isoenzymes of creatine kinase.

One of the important aspects of the present invention is that frozen particles produced using the apparatus and process of this invention retain the biological and chemical characteristics and properties of the liquid product from which they are produced. For example, liquid products containing dissolved proteins such as enzymes can be frozen using the present invention to produce particles which retain the enzymatic activity of the aqueous liquid product.

By "liquid product nozzle" is meant any nozzle which can be used to introduce droplets of liquid product to be frozen into the apparatus of the present invention. The droplets of liquid product can vary depending on the desired frozen particle size. The liquid product nozzle therefore should be chosen so as to provide for droplets of a size sufficient to provide for the desired frozen particles. The preferred particle size range for the frozen particles produced using the apparatus of the present invention is about 75 to 600 μm.

Several types of cryogenic liquid nozzles are suitable for use with the present invention. A cryogenic liquid nozzle which produces a planar such as a flat or curved spray pattern is preferred. An example of a suitable nozzle for use as a cryogenic liquid nozzle is Model #HVV 9510, available from Spraying Systems, Inc.

One of the important features of the present invention is that the cryogenic liquid nozzles 12 are positioned so that they discharge cryogenic liquid to produce a spray pattern which forms an entrapment zone or a curtain around the liquid product droplets 63. The entrapment zone is defined by an interior region formed by a substantially continuous, annular downwardly directed circumferential wall of cryogenic liquid. At least 3 liquid nozzles are required to form the entrapment zone. The entrapment zone formed by 3 cryogenic liquid nozzles is in the shape of a triangle.

Preferably 4 to 6 cryogenic liquid nozzles are used, each nozzle producing a downwardly directed planar spray pattern. The entrapment zone produced using such a preferred spray pattern with four such nozzles is in the shape of a box such as a square or rectangle. FIG. 6 depicts such a configuration.

By forming an entrapment zone around the liquid product droplets 63 the apparatus of the present invention provides for a continuous high yield manufacturing process which can produce frozen particles of a uniform spherical size and homogeneous chemical composition which do not impinge against or adhere to the sides of the apparatus housing 6. The cryogenic liquid nozzle 12 has a slit shaped orifice which (FIG. *4a*), is available with different slit sizes to discharge the cryogenic liquid as a flat or planar spray pattern with the planar portion defining various spray angles.

FIG. 7 illustrates the entrapment zone 97 around the spray solution 63 formed by the cryogenic liquid spray 36.

By "housing" is meant a chamber in which the liquid product droplets are frozen. The housing 6 confines any gaseous cryogen which may have evaporated from the cryogenic liquid. The housing 6 should be vented to allow for the escape of any evaporated gaseous cryogen. A suitable housing 6 for use with the present invention can have a variety of shapes including rectangular, square, and cylindrical shapes. An upper portion of the housing 6 is preferably used for the introduction of the cryogenic liquid and the liquid product droplet 63, and for the formation of the frozen particles. A lower portion of the housing 6 is preferably used for collecting the frozen particles and venting any gaseous cryogen which may have evaporated from the cryogenic liquid. The housing 6 need not be insulated; an uninsulated housing 6 is preferred.

The preferred configuration of the cryogenic liquid nozzles 12 is a plurality of four nozzles positioned in a ring manifold 10. The preferred cryogenic liquid nozzles 12 produce a downwardly directed flat or planar spray pattern. The cryogenic liquid is introduced into the ring manifold 10, shown by 22, through a tube 14. The use of a plurality of nozzles screwed into a manifold for the cryogenic liquid nozzles 12 provides for the introduction of flat streams of cryogenic liquid shown by 36 into the housing 6. These flat sprays of cryogenic liquid should be sufficient to produce the maximum amount of frozen particles for a given amount of liquid product and should provide for a uniform environment of liquid cryogenic droplets and gaseous cryogen within the housing 6 of the apparatus in order to be useful for the continuous manufacturing of frozen particles. The cryogenic liquid spray droplets should be sufficiently small so that cryogenic liquid does not run out the bottom of the housing 6. The formation of an entrapment zone produced by a plurality of cryogenic liquid flat spray, is important for providing for the optimal heat transfer between the cryogenic liquid and the liquid product droplets 63.

Preferably, the temperature at the lower cylinder 28 outlet is maintained at about −100° to about −180° C. This temperature range can be obtained typically by choice of cryogenic liquid, adjustment of cryogenic liquid flow rate, and the sizes and quantity of nozzles. If this temperature range cannot be achieved, the liquid product flow rates can be adjusted so that the liquid product flow rate into the apparatus can be lowered.

Initially the liquid product flow rate can be adjusted to about 300 milliliters per minute (ml/min) and the atomization gas pressure can be adjusted to about 11 pounds per square inch (psi). By adjusting liquid product flow rate and atomization pressure a desired particle size can be achieved. For example, an undesirably small particle size can be corrected by lowering the atomization pressure. Other variables which can be optimized to achieve a desired particle size include cryogenic liquid flow rate, choice of type of liquid product and cryogenic liquid nozzles 12, and choice of housing 6.

Figure 5:
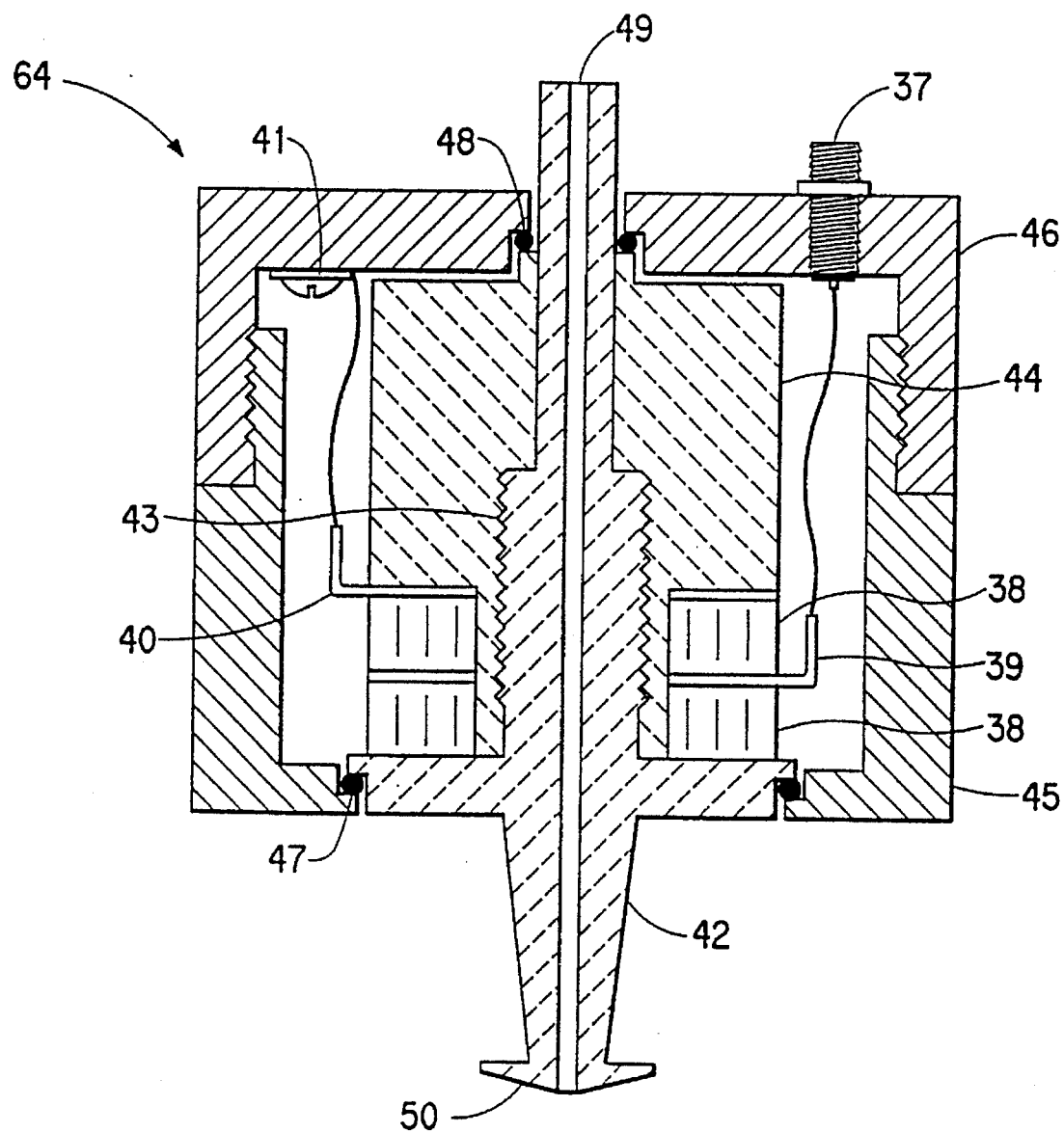
FIG. 5 is another alternative embodiment of the invention depicting an Ultrasonic nozzle which can be used as a liquid product nozzle in the apparatus of FIG. 1.
Figure 6:
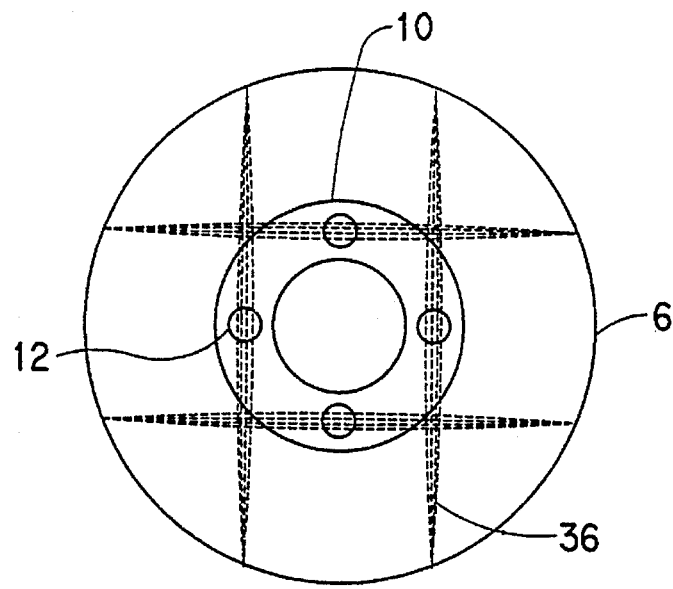
FIG. 6 is a bottom view of the cryogenic liquid nozzles showing the flat planar spray pattern entrapment zone of this invention.
Figure 7:
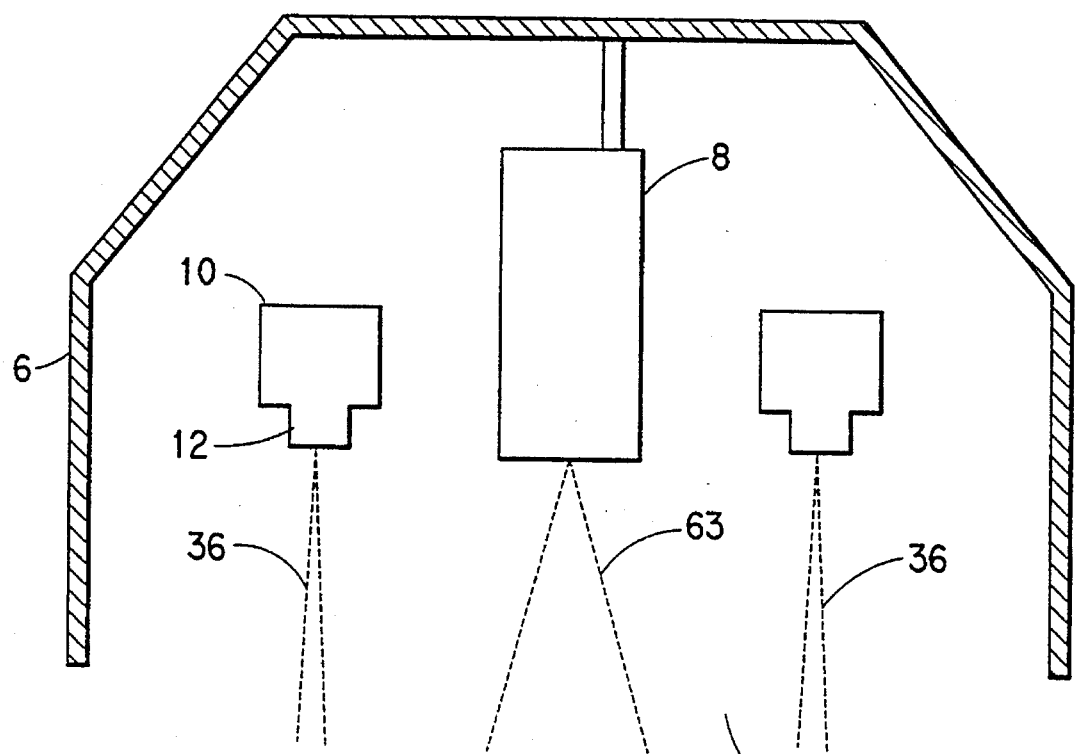
FIG. 7 is a schematic representation of the cryogenic liquid nozzle and product liquid nozzle spray patterns used in this invention.

FIG. 5 depicts a ultrasonic nozzle assembly 64 suitable for use as the liquid product nozzle of the present invention. Such ultrasonic nozzle assemblies 64 are known in the art and are commercially available. Ultrasonic nozzles produce droplets of the liquid product by electrically generated vibrations of the nozzle and are typically useful for producing droplets in the size range of about 10 to about 100 µm. The ultrasonic nozzle assembly 64 has a nozzle 42 with an axially projecting threaded boss 43 and a hollow core 49. A pair of piezoelectric crystals 38, each having an associated electrode 39,40 are received on the boss 43. The crystals 38 are held in place by threading the back piece 44 onto the boss 43. The nozzle 42, crystals 38, electrodes 39,40 and back piece assembly 44 is elastically supported in the threadably engaging front housing 45 and rear housing 46 by the front and rear O-rings, 47 and 48 respectively. An ultra high frequency electrical signal is supplied to the piezoelectric crystal discs 38,39 through the connector 37 to the input electrode 39, with a ground being provided through electrode 40 to the ground lug 41. The electrical signal causes the crystals 38,39 to expand and contract at the electrical excitation frequency, thus calling the nozzle 42 and back piece 44 to vibrate by virtue of their elastic mounting on O-rings 47 and 48. Liquid product that is introduced into the hollow core 49 absorbs some of the vibrational energy. The vibrational energy sets up wave motions in the liquid whose peaks become unstable and break away from the liquid mass beneath, causing a fine mist at the tip of the nozzle 50.

By "cryogenic liquid" is meant any liquid capable of freezing the liquid spray of reagent into particles under atmospheric conditions. Various cryogenic liquids which can be used in the present invention include nitrogen, carbon dioxide, argon and various fluorocarbons. Preferably the cryogenic liquid used is nitrogen.

By "cryogenic liquid nozzle" is meant any nozzle for introducing a cryogenic liquid into the apparatus of the present invention.

EXAMPLE 1

Construction of an Apparatus for Producing Frozen Particles of a Liquid Product

An example of an apparatus designed and built for producing frozen particles of a liquid product in accordance with the present invention consisted of two circular sections and a top plate 30 of FIG. 1 welded to each other.

The lower section was a 14 inch (") diameter, 48" high open-ended vertically disposed lower cylinder FIG. 2 (28). The truncated conical middle section, FIG. 2 (26), had a lower diameter of 14", an upper diameter of 9½", and a height of 10". The top plate, FIG. 1 (30), consisted of an 9½" diameter disk with a 3" diameter hole in its center and a 1.5" baffle, FIGS. 1 and 3 (16), extending downward.

All of the sections including the top plate 30 of the vessel were constructed using 0.125" thick, 304 grade stainless steel and the entire vessel was mounted thru the top of a product collection box (5).

The cryogenic liquid nozzles, FIG. 1, (12), were nozzles screwed into a hollow ring manifold, FIG. 1 (10), with an inside diameter of 3½", an outside diameter of 6", and a 1" by ¾" rectangular shaped cross section using 0.187" thick 304 stainless steel. The cryogenic liquid nozzles (12) were 4 Spray Systems Model 9510, equally spaced around the bottom of a ring manifold, FIG. 1 (10). The nozzles 12 were disposed about the atomization nozzle 8.

The cryogenic liquid was introduced into the housing 6 of the apparatus by forcing it through the hollow interior of the ring manifold 10 and out of the nozzles FIG. 1 (36).

Three equally spaced 1 inch long, ¾ inch diameter vertical posts, FIG. 1 (32), were attached to the top of the ring manifold 10 to support it within the housing 6. The bottom portion of the posts were welded to the ring. The top portion of the posts were drilled and tapped for ¼-20×¾ inch screws which provided a means for centrally mounting the ring manifold 10 to the top plate 30 of the vessel. A conventional bulk head fitting (not shown) was also attached to the top of the ring manifold 10 which allowed a one-half inch diameter cryogenic liquid feed line, FIGS. 1 and 3 (14), to be attached to and supply cryogenic liquid, FIGS. 1, 2, and 3 (22), to the hollow interior of the ring manifold 10.

The liquid product nozzle was a pneumatic atomization nozzle FIG. 1 (8), with a 1.1 millimeter (mm) opening, (Model SU-5, Spraying Systems, Inc.). The atomization nozzle 8 was centrally mounted using a cross-bar in the central hole of the upper plate 30 such that the tip of the atomization nozzle 8 was even with the tips of the cryogenic liquid nozzles (12). A peristaltic pump (pump model no. 7520-00, Master Flex Co.) was used to feed the liquid product to the atomization nozzle 8.

EXAMPLE 2

Producing Frozen Particles of A CKMB Diagnostic Reagent Useful in a Creatine Kinase-MB (CKMB) Immunoassay Into a 10 liter (L) stainless steel pot was added 1703 milliliters (ml) of deionized water. The following components were added, mixed, and allowed to dissolve in order: 360 trehalose (Sigma AF, St. Louis, Mo.), 95 polyethylene glycol (PEG 8000) (Sigma AF, St. Louis, Mo.), 215 bovine albumin (Miles Inc., Kankakee, Ill.), 252 sodium chloride (VWR Scientific, Bridgeport, N.J.), 1.8 g magnesium chloride (VWR Scientific, Bridgeport, N.J.), 254 disodium PIPES buffer, (Research Organics, Inc., Cleveland, Ohio), 39 PIPES (Research Organics Inc., Cleveland, Ohio), 125 ml of a CKMB conjugate solution consisting of 1:1 ratio of F(ab')2 anti-CKMB antibody fragments and β-galactosidase (prepared as described below), and 1.1 g mouse IgG antibody (Scantibodies Laboratory, Santtee, Calif.) to eliminate non specific binding.

The cell lines producing the monoclonal antibodies employed were obtained using the procedure described in U.S. Pat. No. 4,912,033 and in Vaidya et al., Clin. Chem. 32(4): 657–663 (1986), the disclosures of which are hereby incorporated by reference.

The anti-CKMB monoclonal antibodies so obtained were purified and isolated using affinity chromatography on Protein A Sepharose (Pharmacia Fine Chemicals, Uppsala, Sweden). Protein A is a polypeptide (MW 42,000) isolated from Staphylococcus aureus which binds immunoglobin without interacting with the antigen binding site.

While the above described method is preferred, monoclonal antibodies can be purified using any number of standard techniques such as ammonium sulfate precipitation dialysis, affinity chromatography, ion exchange chromatography etc. These and other methods for the isolation and purification of monoclonal antibodies are described in general by Goding, Monoclonal Antibodies: Principles and Practice, Academic press, London and New York, 1983 and in U.S. Pat. No. 4,533,496 the disclosures of which are hereby incorporated by reference.

The anti-CKMB monoclonal antibody used to produce the immunoreactive fragment described below was obtained as described above. The clone number was 2580 CC 4.2, and the monoclonal antibody was an IgG2b subclass.

The purified anti-CKMB monoclonal antibody was dialyzed overnight at 4 degrees C. (°C.) against an acetate buffer containing 100 millimolar (mM) sodium acetate and 150 mM sodium chloride, pH. 3.5. The dialyzed antibody solution was diluted to a concentration of 5 milligrams per milliliter (mg/ml) using the acetate buffer. The antibody solution was placed in a water bath at 37° C. for about 5 to 10 minutes.

A 10 mg/ml solution of pepsin (Sigma Chemical Co., St. Louis, Mo.) was prepared in the acetate buffer. The amount of pepsin required to give a weight ratio of antibody to pepsin of 50:1 was determined and the determined amount of pepsin solution was added to the antibody solution as the antibody solution was stirred. The mixture was incubated for about 10–15 minutes. The reaction was then stopped by slowly adding 3.5 molar (M) Tris base drop wise until the pH of the solution was in the range of 7.0 to 8.0. The resulting F(ab')2 preparation was then passed through 15–20 ml of Sepharose having Protein A bound to it in a 2.2×25 centimeter (cm) column at a flow rate of about 4–4.5 ml per hour. The protein peak was monitored by recording the absorbance of the fractions at 280 nm. The protein peak was collected and concentrated to about 30 mg/ml using an Amicon stirred cell fitted with a 62 mm PM 30 membrane filter (both purchased from the Amicon Corp.). The sterilized F(ab'2) concentrate was filtered and stored at −20° C.

The sterilized F(ab')2 concentrate was coupled to β-galactosidase conjugate using the procedure substantially as described by Kitagawa et al., Enzyme labeling with N-hydroxysuccinimidyl ester of maleimide in "Enzyme Immunoassays, Ishikawa et al., Eds., pp 81–90 (1981), the disclosure of which is hereby incorporated by reference. Anti-CKMB monoclonal antibody F(ab')2 fragment was dialyzed against an antibody dialysis buffer containing 20 mM phosphate buffer, 300 mM NaCl, pH 7.0). One mole of F(ab')2 was mixed with 30 moles of N-succinimidyl, 4 (N-maleimido methyl) cyclohexane-1-carboxylate (SMCC) and incubated at room temperature for 35 min. with constant stirring. The mixture was loaded On a Sephadex G-25 column (2.2×13 cm) equipped with the UV detector (absorbance 280 nm). The activated F(ab')2 fragment was eluted using the antibody dialysis buffer. The protein peak was collected, its volume recorded and the protein concentration estimated. One mole of $E.\ coli$ β-galactosidase (Boehringer Mannhelm) equivalent to 1 mole of SMCC activated F(ab')2 was dissolved in the antibody dialysis buffers. Activated F(ab')2 was mixed with β-galactosidase and incubated for at least 25 minutes at 25° C. with constant stirring. Synthesis of the conjugate was monitored using an HPLC (LKB) equipped with a 100 μl loop GF 450 analytical column. The reaction was quenched when the leading peak extended beyond the second peak on the chromatogram by adding 10 μl of 0.1M N-ethylmaleimide solution for every ml of conjugate reaction mixture. The mixture was concentrated to 4.0 ml using an Amicon stir cell and YM 100 filter (both purchased from the Amicon Corp.). Conjugate concentrate was filtered through 0.2μ syringe filter and purified using LKB HPLC equipped with 1 ml loop GF 450 column, UV monitor, fraction collector and chart recorder. Appropriate fractions were collected and pooled and absorbance was measured at a wavelength of 280 nm to estimate the protein concentration. The resulting concentrate was filtered, sterilized and stored at 40° C. Conjugate concentrate was diluted as needed in a β-galactosidase conjugate dilution buffer (33.5 g PIPES (piperazine-N, N'-bis (2-ethanesulfonic acid)) 0.2 g MgCl$_2$, 29.2 g NaCl, 100 g bovine serum albumin, and 0.167 g mouse IgG per liter of deionized water, pH 7.0) for the CKMB assay.

The solution was adjusted to a final volume of 4.8 L with deionized water and filtered through a 5 μm filter (Gelman Sciences, Annarbor Mich. (product No. T 505141).

Liquid nitrogen from a 60,000 pound (lb.) tank was fed through a one-half inch diameter flexible steel tube at flow rate of 3.2 kilograms per minute (Kg/min) to the ring manifold having the cryogenic liquid nozzles (12). Liquid nitrogen was thereby forced out of the cryogenic liquid nozzles. A steady state temperature measured centrally at the extreme bottom of the housing 6 was in the range of −150 to −170 degrees C. (°C.). An 18 inch square 2.0 inch deep collection tray FIG (2) 34 was pre-chilled to −35° C. and placed about 2" below the opening of the vessel.

Nitrogen gas at a pressure of 10 pounds per square inch (psi), FIGS. 1, 2, and 3 (20), and at a flow rate of 300 milliliters per minute (ml/min), was fed to the atomization nozzle.

Frozen particles were collected in the collection tray 34 and manually distributed in the tray 34 to form a uniformly thick layer of frozen liquid product particles about ⅝" deep. The liquid product and nitrogen gas flows to the atomization nozzle were stopped and the production run of frozen particles was completed.

The average particle size was determined to be 402 microns by filtering the particles through a series of known size sieves, with the size distribution shown in Table 1.

TABLE 1

| Size (microns) | % of total particles |
| --- | --- |
| >590 | 16.4 |
| 505–590 | 19.6 |
| 335–504 | 25.2 |
| 215–334 | 10.8 |
| 165–215 | 7.6 |
| 110–164 | 14.0 |
| 75–109 | 6.4 |

β-galactosidase activity of the above liquid product was measured both before and after spray freezing using the aca® discrete clinical analyzer (E. I. dupont de Nemours and Company, Wilmington, Del. 19898). The pre spray freezing sample was obtained by diluting 1 mL of the liquid product with 20 mL of water. A post freezing sample was obtained by dissolving 1 gm of the frozen liquid product in 4 mL of water and diluting this solution with 80 mL of water. The prepared samples were placed in standard aca sample cups. The sample cups along with 3 aca MCKMB packs (standard aca® discrete clinical analyzer packs available from E. I. Du Pont de Nemours and Company, Wilmington, Del.) were loaded on the aca. The aca dispensed 100 μl of sample, 2 mL of phosphate buffer, pH 7.8, and 2.9 mL of water into each MCKMB pack. Breaker mixer 1, a component of the aca® discrete clinical analyzer which breaks tablet reagents in the pack and facilitates the mixing of the reagents, was utilized to dissolve and mix the pack reagents with the sample. Bound enzyme reacted with chlorophenol red galactoside (CPRG) contained in the pack reagents at 37° C. to form chlorophenol red (CPR). After 4.2 minutes the absorbance of the contents of the pack was measured at 577 and 600 nm wavelengths. 577 was the primary wavelength at which the CPR has maximum absorbance, and 600 nm was the blanking wavelength. The 600 nm reading was subtracted from the 577 reading to eliminate interference due to suspended particles and the resulting average absorbance number was multiplied by 20 due to the 1 to 20 dilution of the sample. The results, indicated minimal loss of enzymatic activity due to spray freezing. Thus, the usefulness of the present invention in producing frozen particles of diagnostic reagents which retain their biological activity upon freezing has been demonstrated.

What is claimed is:

1. An apparatus for utilizing a cryogenic liquid for producing frozen particles of a liquid product which comprises:
   (a) a housing;
   (b) means positioned in the housing including at least three cryogenic liquid nozzles for producing a substantially continuous, annular downwardly directed circumferential wall of cryogenic liquid defining an interior entrapment zone;
   (c) a liquid product nozzle positioned in the housing for introducing droplets of the liquid product into the entrapment zone whereby the cryogenic liquid freezes the liquid product droplets to product frozen particles; and
   (d) a baffle located between the liquid product nozzle and the plurality of cryogenic liquid nozzles to shield the liquid nozzle and to prevent freezing of the liquid product in the liquid nozzle.

2. The apparatus of claim 1 wherein the liquid product nozzle is an atomization nozzle.

3. The apparatus of claim 1 wherein the liquid product nozzle is an ultrasonic nozzle.

4. The apparatus of claim 1 wherein the cryogenic liquid nozzles are positioned in a ring manifold and produce a planar spray pattern.

5. The apparatus of claim 1 wherein the housing comprises an upper plate having an upper diameter, and a vertically disposed cylinder having a diameter larger than the upper diameter, the upper plate and the cylinder connected by a truncated conical section.

6. The apparatus of claim 1 wherein the apparatus has a collection means below the liquid product nozzle for the frozen particles.

7. The apparatus of claim 1 wherein the entrapment zone is box-shaped.

8. A process for utilizing a cryogenic liquid for producing frozen particles of a liquid product in a housing which comprises the steps of:
   (a) introducing the cryogenic liquid into the housing in an annular, downward direction creating an substantially continuous downwardly directed circumferential wall of cryogenic liquid, defining an interior entrapment zone; and
   (b) introducing droplets of the liquid product into the entrapment zone,
   whereby the cryogenic liquid freezes the liquid product droplets to produce frozen particles.

9. The process of claim 8 wherein the liquid product is an aqueous solution.

10. The process of claim 9 wherein the aqueous solution contains proteins.

11. The process of claim 8 wherein the liquid product particles have a diameter of about 75 to 590 microns.

12. The process of claim 8 wherein the liquid product particles are spherical.

13. The process of claim 8 wherein the cryogenic liquid is applied by disposing the cryogenic liquid circumferentially about the liquid product droplets.

* * * * *